(12) United States Patent
Painchaud et al.

(10) Patent No.: US 8,616,418 B2
(45) Date of Patent: Dec. 31, 2013

(54) LIQUID DISPENSING DEVICE EQUIPPED WITH A SEALING COMPONENT

(75) Inventors: Gaetan Painchaud, Francheville (FR); Guillaume Grevin, L'Isle d'Abeau (FR); Xavier Julia, Villefontaine (FR); Sylvain Lanzi, Chirens (FR)

(73) Assignee: Rexam Healthcare la Verpilliere (FR)

( * ) Notice: Subject to any disclaimer, the term of this patent is extended or adjusted under 35 U.S.C. 154(b) by 540 days.

(21) Appl. No.: 12/580,067

(22) Filed: Oct. 15, 2009

(65) Prior Publication Data

US 2010/0116852 A1    May 13, 2010

(30) Foreign Application Priority Data

Oct. 15, 2008    (FR) ...................................... 08 05716

(51) Int. Cl.
*B65D 47/18*    (2006.01)

(52) U.S. Cl.
USPC ........... 222/422; 222/212; 222/213; 222/420; 222/496

(58) Field of Classification Search
USPC ......... 222/490–496, 212–215, 420–422, 518, 222/511, 209, 498, 499, 513, 514
See application file for complete search history.

(56) References Cited

U.S. PATENT DOCUMENTS

| | | | |
|---|---|---|---|
| 1,697,725 A * | 1/1929 | Guerin | 222/422 |
| 1,941,520 A | 1/1934 | Wiegandt | |
| 3,323,692 A * | 6/1967 | Cook | 222/422 |
| 5,024,355 A * | 6/1991 | Jouillat et al. | 222/162 |
| 5,154,325 A | 10/1992 | Ryder et al. | |
| 5,183,184 A * | 2/1993 | Ranalletta et al. | 222/189.09 |
| 5,197,638 A * | 3/1993 | Wood | 222/212 |
| 5,685,869 A * | 11/1997 | Py | 604/294 |
| 6,145,707 A * | 11/2000 | Baudin | 222/189.09 |
| 6,257,503 B1 * | 7/2001 | Baudin | 239/337 |
| 6,308,867 B1 * | 10/2001 | Wolter | 222/321.6 |
| 6,336,574 B1 | 1/2002 | Hins | |
| 6,497,346 B1 * | 12/2002 | Dubois et al. | 222/494 |
| 6,840,410 B2 * | 1/2005 | Dark | 222/481.5 |
| 7,303,098 B2 * | 12/2007 | Backes | 222/212 |
| 7,490,744 B2 * | 2/2009 | Matsumoto et al. | 222/494 |
| 2005/0173468 A1 * | 8/2005 | Matsumoto et al. | 222/494 |
| 2006/0261098 A1 * | 11/2006 | Nilsson | 222/496 |
| 2010/0096416 A1 * | 4/2010 | Painchaud et al. | 222/496 |
| 2011/0155770 A1 * | 6/2011 | Painchaud et al. | 222/422 |
| 2012/0223106 A1 * | 9/2012 | Painchaud et al. | 222/422 |

(Continued)

FOREIGN PATENT DOCUMENTS

EP    0602019 A2    6/1994
EP    1052023 A1    11/2000

(Continued)

OTHER PUBLICATIONS

French Search Report; FR 0805716; May 6, 2009; 2 pages.

(Continued)

*Primary Examiner* — Frederick C Nicolas
(74) *Attorney, Agent, or Firm* — St. Onge Steward Johnston & Reens LLC

(57) ABSTRACT

A liquid dispensing device including a sealing component which can take up a liquid release position and a liquid blocking position. The sealing component includes an elastomer part and a rigid part, these parts being fastened to each other when moving.

14 Claims, 1 Drawing Sheet

(56) References Cited

U.S. PATENT DOCUMENTS

2012/0296291 A1* 11/2012 Painchaud et al. ............ 604/298
2012/0305599 A1* 12/2012 Painchaud et al. ....... 222/189.06
2013/0140225 A1* 6/2013 Decock et al. ............. 210/321.6

FOREIGN PATENT DOCUMENTS

| | | | |
|---|---|---|---|
| JP | 2543816 | B2 | 10/1996 |
| JP | 2006500980 | A | 1/2006 |
| JP | 2008174268 | A | 7/2008 |
| WO | 9212065 | A1 | 7/1992 |
| WO | 2005010413 | A2 | 2/2005 |
| WO | 2005046541 | A2 | 5/2005 |

OTHER PUBLICATIONS

Japanese Patent Office, Notice of Reasons for Rejection, Application No. 2009-238609, Mailing Date: Oct. 1, 2013, 3 pages.

* cited by examiner

LIQUID DISPENSING DEVICE EQUIPPED WITH A SEALING COMPONENT

CROSS-REFERENCE TO RELATED APPLICATIONS

The present application claims priority of French patent application No. 0805716 filed on Oct. 15, 2008, the content of which is incorporated herein by reference.

FIELD OF THE INVENTION

This invention relates to the technical field of dispensing liquid, in particular, but not exclusively, dispensing liquid in drop form, such as ophthalmic liquid.

BACKGROUND OF THE INVENTION

Devices implementing this type of dispensing are already known in the state of the art. According to an example described in document EP 0 602 019, the device may comprise a valve forming a seal, made from an elastomer material, and which can take up in the device a liquid release position and a liquid blocking position. More precisely, this valve takes up its liquid release position under the effect of a pressure exerted by the user on the device bottle.

This invention seeks in particular to propose a dispensing device in which the sealed component in its blocking position blocks the liquid more reliably.

SUMMARY OF THE INVENTION

The invention therefore relates to a liquid dispensing device comprising a sealing component which can take up a liquid release position and a liquid blocking position, wherein the sealing component comprises an elastomer part and a rigid part, these parts being fastened to each other, in particular when moving.

An "elastomer part" is taken to mean a part comprising or made from an elastomer material. The elastomer part and the rigid part are made from different materials, the elastomer part being more elastic than the rigid part. In addition, it is understood that the sealing component defined above seals the device. It could also be referred to as a "sealing valve".

The inventors therefore had the idea of designing a sealing component which is made not completely of an elastomer material but which comprises an elastomer part associated with a rigid part. The resulting sealing component has a behaviour more constant over time, guaranteeing better sealing for the device. With a valve made completely from elastomer, the elastomer material has been observed to exhibit a certain degree of creep or relaxation over time, thereby compromising the valve sealing efficiency.

In addition, this creep or relaxation increases when mechanical stress is exerted on the valve to make it take up its liquid blocking or release position. Thus, thanks to the rigid part on the sealing component, the stress can be exerted on the rigid part, this stress being transmitted to the elastomer part, while avoiding creep or any other deformation of the elastomer material due to contact between the source of the stress and the elastomer. In addition, greater stress can be exerted on the sealing component due to the presence of the rigid part. If the sealing component is made completely from elastomer material, in fact, it is difficult to exert a high pressure on the sealing component, since this pressure may not only damage the sealing component but may also be attenuated by the elastomer material, and therefore lose its intensity.

Note also that the sealing component proposed seals more easily than if it was made completely from a relatively rigid material which is pressed. In this case, in fact, a very high stress must be exerted on the sealing component for it to seal. In this case, thanks to the elastomer part which provides the seal, less stress can be exerted.

Use of both a rigid material and an elastomer material offers the advantages of both materials while reducing the disadvantages inherent to each one.

The device may also comprise one or more of the following characteristics.

The elastomer part comprises an elastomer material such as a thermoplastic elastomer, for example the material sold under the brand name "Santoprene", or a material such as silicone, much appreciated for its low-deformation properties over time.

The rigid part is preferably made from a thermoplastic material not likely to deform under the effect of a stress such as those exerted in the liquid dispensing device, for example polypropylene (PP), high-density polyethylene (HDPE) and polybutylene terephthalate (PBT).

The elastomer part and the flexible part are assembled by overmoulding, welding, gluing, clipping or riveting. Nevertheless, any other assembly means which could be used to fasten these parts together permanently could be considered.

The device comprises a return element, exerting a return force on the sealing component so that it takes up its liquid blocking position, the return element preferably resting against or being fixed to the rigid part of the sealing device. The rigid part therefore takes the stress of the return element on the sealing component, so that this stress is not exerted directly on the elastomer part, which could deform it. Preferably, direct pressure is exerted on the rigid part.

The return element is either a spring, possibly a helical spring, an elastic strip, or an element made from an elastomer material. This return element could be made from a metallic or a non-metallic material.

The return element is made in one piece with the elastomer part or the rigid part of the sealing component, or with another functional part of the nozzle, for example an envelope of the nozzle. The return element can therefore be integrated directly in one of these parts, which offers the advantage of reducing the number of parts in the device.

The sealing component, preferably its rigid part, comprises means for forming liquid drops. The sealing component is therefore used to produce liquid drops, which offers the advantage of not having to provide such means on another part separate from the sealing component, and therefore having to provide a seal between the sealing component and the drop formation means. Note that the drop formation means may consist of a flared part, into which a liquid dispensing channel made in the elastomer part opens out, this flared shape, for example a cone, preventing the drop coming out as a jet.

The rigid part covers the elastomer part over a large proportion of the surface of the elastomer part. Thus, the rigid part acts as a type of lining for the elastomer part, which in particular distributes an occasionally exerted stress over the entire surface of the rigid part, therefore of the elastomer part. The elastomer part is therefore rarely subjected to local stresses and is less likely to deform.

The elastomer part comprises a zone not covered by the rigid part, thereby allowing this zone to extend elastically, for example so that the sealing component can take up its liquid release position.

The elastomer part and the rigid part each have the overall shape of a hat with a central cylindrical shape extended by an edge to attach the component to the nozzle.

In its liquid blocking position, the elastomer part cooperates with pressing means, these pressing means being formed on an inner core of the device, possibly as a projection. The liquid is blocked by the cooperation between the elastomer part and these pressing means.

BRIEF DESCRIPTION OF THE DRAWINGS

The invention will be better understood from the following description, given solely by way of example and by referring to the drawings wherein.

DETAILED DESCRIPTION OF THE INVENTION

Figure 1:
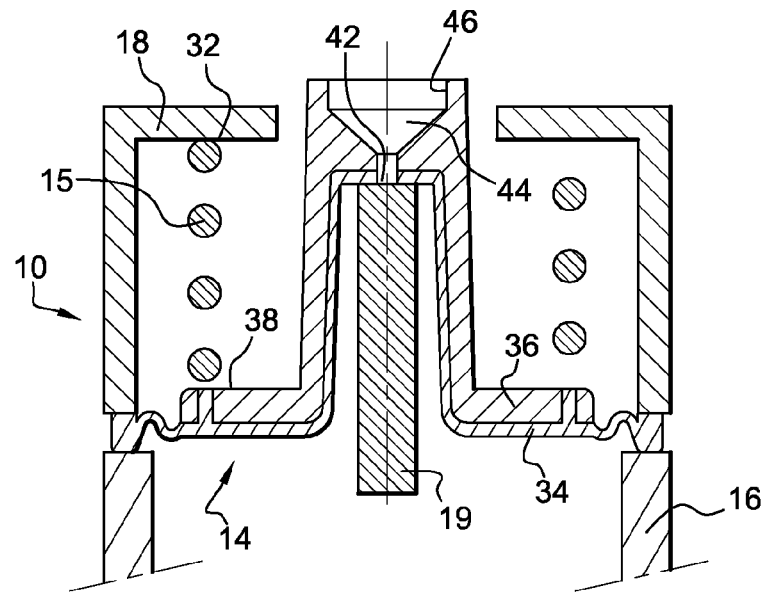
FIG. 1 is a diagrammatic view functionally illustrating a device according to one embodiment of the invention.

A liquid dispensing device comprises a nozzle 10, represented partially and schematically on FIG. 1, designed to be attached to a plastic reservoir containing the liquid to be dispensed. The device can be used to dispense predetermined liquid doses, more precisely drops of liquid, intended for ocular, nasal or oral application, for example, collyrium drops for the eyes.

Figure 2:
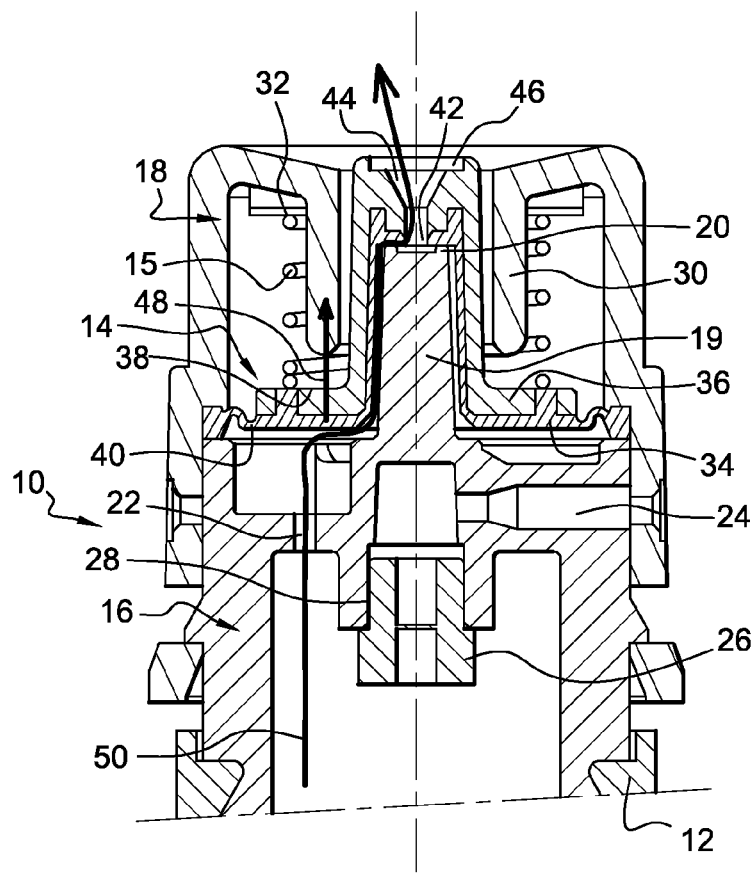
FIG. 2 is a longitudinal sectional view illustrating an example of device as schematised on FIG. 1.

As can be seen on FIG. 2, the nozzle 10 if fitted on the neck 12 of the reservoir, this reservoir being intended to be pressed by the user to make the liquid come out, as described in the remainder of this document. In addition, the nozzle 10 is covered by a closure cap, not shown on the figures. In this example, the reservoir is made of plastic and is intended to be pressed by the user to make the liquid come out. Other types of reservoir could also be considered, in particular made of glass or metal, the user being able to release liquid by an action other than pressing it, for example by pressing on a pump activation element.

The nozzle 10 comprises a sealing component 14, arranged between a first part 16 and a second part 18 of the nozzle 10, and a return element 15.

The first part 16 is an inner core 16, comprising a substantially cylindrical protuberance 19 projecting from the distal end of the core 16. On its distal end, this protuberance 19 supports means 20 for pressing on the sealing component 14, these means 20 being in this example composed of a projection forming an annular flange designed to press on the sealing component 14. As an alternative, the means 20 may be formed directly by the distal end of the protuberance 19, or take other shapes. The inner core 16 also comprises a channel 22 for the liquid to flow from the reservoir to the outside of the device, as well as a part connecting the core 16 to the reservoir 12. The nozzle 10 also comprises venting means, designed to allow air to enter the reservoir to make up for the depression generated by the pressure exerted by the user to make liquid come out. In this example, the venting means are supported by the inner core 16 and comprise an air channel 24, crossed by a hydrophobic filter 26, designed to filter the incoming air without, however, allowing liquid to escape via the channel 24. More precisely in this example, the filter 26 is arranged in a filter housing 28, this housing 28 consisting of an annular groove arranged in the centre of the inner surface of the core 16, in which the filter 26 is fitted.

The second part 18 of the nozzle 10 corresponds, in this example, to an outer upper envelope of the nozzle 10. This outer envelope 18 is designed to cover the inner core 16, the sealing component 14 (at least partially) and the spring 15. More precisely, it comprises an open inner protuberance 30 formed by a central annular groove, designed to surround the distal end of the protuberance 18 and the sealing component 14 allowing liquid to come out of the device. The envelope 18 also comprises a seat 32 to support the return element 15, this seat 32 being arranged around the protuberance 30.

The sealing component 14 may take up a liquid blocking position, illustrated on FIGS. 1 and 2, preventing liquid from returning once it has left the sealed zone, and a liquid release position (not shown). The component 14 comprises an elastomer part 34 and a rigid part 36, parts 34 and 36 being fastened to each other, in particular when moving, which means that when part 34 is displaced, part 36 is displaced with it, and vice versa. In this example, parts 34 and 36 are assembled by overmoulding, but other types of assembly could be considered. The elastomer part 34 is made from an elastomer material such as silicone or a thermoplastic elastomer material. The rigid part 36 is made from a thermoplastic material such as polypropylene. The rigid part 36 comprises a bearing surface 38 for the return element 15. As can be seen on the figures, the rigid part 36 covers the elastomer part 34 over substantially its entire surface, a zone 40 of the elastomer part nevertheless being left free at the end of the elastomer part, to allow this elastomer part 34 to extend. More precisely, the elastomer part 34 and the rigid part 36 each have the shape of a hat with a central cylindrical shape, of shape substantially complementary to that of the protuberance 19 of the core 16, this cylindrical shape being extended on its proximal end by an edge, one of the edges being used to attach the component 14 to the nozzle. In the example described, the edge of the elastomer part 34 is attached, at its periphery 40, to the rest of the nozzle 10. The rigid part 36 therefore covers the elastomer part 34 over a large proportion of its surface, except around its periphery 40. As can be seen on the figures, parts 34, 36 define a channel 42, arranged on the bottom of their central cylindrical shape, allowing the liquid to come out. Moreover, the rigid part 36 comprises means 44 for forming liquid drops. More precisely, these means 44 have the shape of a cone starting from the channel 42 and widening towards the distal end of the device, so as to form a drop and avoid the liquid being dispensed in a jet, cone 44 leading out onto a cylindrical portion 46, used to calibrate the drop.

In this example, the return element 15 is a helical metallic spring. This element 15 exerts a return force on the sealing component 14, by pressing on the bearing surface 38 of the rigid part 36, so as to return the sealing component 14 to its liquid blocking position.

As can be seen on the figures, the sealing component 14 is sealed (static sealing) between the two parts 16, 18, so that liquid flowing through the channel 22 does not escape inside the envelope 18.

The operation of the dispensing device will now be described.

To dispense the liquid drops, the user presses the device reservoir, making liquid flow into the channel 22 and therefore exerting a pressure on the elastomer part 34. Under the effect of this pressure, the sealing component moves from its liquid blocking position to its liquid release position, making a translation upwards, as shown by the arrow 48. More precisely, the zone 40 of the elastomer part 34 deforms, by extending, to allow this upward displacement of the elastomer part. After this displacement, the seal provided by cooperation of the pressing means 20 with the sealing component 14 is broken, and liquid can flow through the channel 42 up to parts 44, 46, to form a liquid drop. The liquid path is illustrated by the arrow 50. Once the drop has been released, the user no longer needs to press on the reservoir which fills with air through channel 24. In addition, since the pressure of the liquid coming out has stopped, the sealing component 14 returns to its liquid blocking position under the effect of the return force provided by element 15. The pressing means 20 and the elastomer part of the component 14 therefore cooperate again to prevent liquid from coming out.

Note that the invention is not limited to the previously described examples. In particular, the return element is, in the embodiment described, a helical spring, but other types of return element could be considered, made from metal or not, such as a rubber strip or an elastomer element. In particular, this return element 15 could be integrated directly in the envelope 18 of the nozzle 10, or in the sealing component 14, being integrated either in the elastomer part 34 or in the rigid part 36. Integrating this element 15 in another functional part therefore reduces the number of pieces to be assembled.

The advantages of the dispensing device have been described above. Note in particular that the rigid part 36 forms a kind of shell for the elastomer part 34, making it easier to exert stress on the sealing component, without risk of deforming it.

What is claimed is:

1. A device for dispensing liquid in drop form, characterized in that the device comprises a nozzle comprising:
    a sealing component which can take up a liquid release position and a liquid blocking position, and
    a pressing element for pressing on the sealing component;
    wherein the sealing component comprises an elastomer part and a rigid part, the elastomer part, in the liquid blocking position, cooperating with said pressing element to provide a seal, the elastomer part and the rigid part being fastened to each other such that when the elastomer part of the sealing component moves the rigid part moves together with the elastomer part,
    wherein exertion of pressure of the liquid on the sealing component causes the sealing component to move from the liquid blocking position to the liquid release position to allow liquid to be dispensed;
    wherein in the liquid release position, the seal between the pressing element and the sealing component is broken; and
    wherein the sealing component comprises parts for forming liquid drops, the parts for forming drops having the shape of a cone widening towards a distal end of the device.

2. The device according to claim 1, wherein the elastomer and rigid parts are assembled by overmoulding, welding, gluing, clipping or riveting.

3. The device according to claim 1, wherein the parts for forming liquid drops is formed in the rigid part.

4. The device according to claim 1, wherein the rigid part covers the elastomer part over a large proportion of a surface of the elastomer part.

5. The device according to claim 4, wherein the elastomer part comprises a zone not covered by the rigid part.

6. The device according to claim 1, wherein the elastomer part and the rigid part each have an overall shape of a hat with a central cylindrical shape, extended at one end by an edge, one of the edges being used to attach the component to the nozzle.

7. The device according to claim 1, wherein the pressing element is formed on an inner core of the device as a projection.

8. A device for dispensing liquid in drop form, characterized in that the device comprises a nozzle comprising:
    a sealing component which can take up a liquid release position and a liquid blocking position, and
    a pressing element for pressing on the sealing component;
    wherein the sealing component comprises an elastomer part and a rigid part, the elastomer part, in the liquid blocking position, cooperating with said pressing element to provide a seal, the elastomer part and the rigid part being fastened to each other, at least when moving,
    wherein exertion of pressure of the liquid on the sealing component causes the sealing component to move from the liquid blocking position to the liquid release position to allow liquid to be dispensed; and
    wherein the sealing component comprises parts for forming liquid drops, the parts for forming drops having the shape of a cone widening towards a distal end of the device;
    the device further comprising a return element, exerting a return force on the elastomer part so that the sealing component takes up the liquid blocking position, the return element resting against or being fixed to the rigid part of the sealing device.

9. The device according to claim 8, wherein the return element is either a helical spring, an elastic strip, or an element made from an elastomer material.

10. The device according to claim 8, wherein the return element is made in one piece with the elastomer part or with the rigid part of the sealing component, or with another functional part of the nozzle.

11. The device according to claim 10, wherein the return element is made in one piece with an envelope of the nozzle.

12. A device for dispensing liquid in drop form, characterized in that the device comprises a nozzle comprising:
    a sealing component comprising an elastomer part and a rigid part, said sealing component moveable between a liquid release position and a liquid blocking position, and the elastomer part and the rigid part being fastened to each other such that when the elastomer part of the sealing component moves the rigid part moves together with the elastomer part; and
    a core having a side surface and a distal end surface;
    wherein, in the liquid blocking position, a surface of the elastomer part of the sealing component cooperates with the distal end surface of said core to provide an annular seal;
    wherein in the liquid release position, the seal between the pressing element and the sealing component is broken; and
    wherein the sealing component comprises parts for forming liquid drops, the parts for forming drops having the shape of a cone widening towards a distal end of the device.

13. The device according to claim 12, wherein said core has a cylindrical shape.

14. The device according to claim 13, wherein the elastomer part and the rigid part each have the overall shape of a hat with a central cylindrical opening in which is disposed said core.

* * * * *